US006835398B2

(12) United States Patent
Cohen

(10) Patent No.: US 6,835,398 B2
(45) Date of Patent: Dec. 28, 2004

(54) METHOD OF ADMINISTERING HIGH-DOSE, ORAL MAGNESIUM FOR TREATMENT OF CHRONIC PAIN SYNDROME OF ERYTHROMELALGIA

(76) Inventor: Jay S. Cohen, 13622 Nogales Dr., Del Mar, CA (US) 92014

( * ) Notice: Subject to any disclaimer, the term of this patent is extended or adjusted under 35 U.S.C. 154(b) by 253 days.

(21) Appl. No.: 10/292,639

(22) Filed: Nov. 12, 2002

(65) Prior Publication Data

US 2003/0091655 A1 May 15, 2003

Related U.S. Application Data

(60) Provisional application No. 60/334,729, filed on Nov. 15, 2001.

(51) Int. Cl.[7] ..................... A61K 31/19; A61K 33/06; A61K 33/08; A61K 33/10; A61K 33/12
(52) U.S. Cl. ..................... 424/681; 424/457; 424/468; 424/601; 424/682; 424/683; 424/686; 424/688; 424/689; 424/692; 424/697; 424/722; 514/557; 514/558; 514/560; 514/561; 514/568; 514/574; 514/867; 514/905; 514/964
(58) Field of Search ..................... 424/457, 468, 424/601, 681–683, 686, 688, 689, 692, 697, 722; 514/557, 558, 560, 561, 568, 574, 867, 905, 964

(56) References Cited

U.S. PATENT DOCUMENTS

| RE34,222 E | * | 4/1993 | Bloch ........................... 514/25 |
| 5,654,011 A | * | 8/1997 | Jackson et al. ............. 424/635 |
| 5,914,129 A | * | 6/1999 | Mauskop .................... 424/464 |
| 6,159,505 A | * | 12/2000 | Piper ........................... 424/679 |
| 6,218,192 B1 | * | 4/2001 | Altura et al. ................. 436/79 |
| 6,500,450 B1 | * | 12/2002 | Hendrix ....................... 424/439 |

OTHER PUBLICATIONS

Kvernebo, K. "Erythromelalgia: A Condition Caused by Microvascular Arteriovenous Shunting." *VASA*, Nov. 1998; Supplement 51:1–40.
*Drug Facts and Comparisons*, Facts and Comparisons, Chapter 1, Nutritional Products, a Wolters Kluwer Company, St. Louis, 1993–1997.
Mangat, H.S., "Nebulized Magnesium Sulphate Versus Nebulized Salbutamol in Acute Bronchial Asthma: A Clinical Trial", *European Respiratory Journal*, Aug. 1998, 12(2):341–4.
Sueta, C.A. et al, "Antiarrhythmic Action of Pharmacological Administration of Magnesium in Heart Failure: A Critical Review of New Data", *Magnesium Research*, Dec. 1995, 8(4):389–401.
Saris NE; Mervaala E; Karppanen H; Khawaja JA; Lewenstam A. Magnesium. An update on physiological, clinical and analytical aspects. *Clinica Chimica Acta*, Apr. 2000, 294(1–2):1–26.

Mauskop, A. et al., "Intravenous Magnesium Sulfate Rapidly Alleviates Headaches of Various Types", *Headache*, Mar. 1996, 36(3):154–60.
Mauskop, A., "Role of Magnesium in the Pathogenesis and Treatment of Migraines", *Clinical Neuroscience*, 1998, 5(1):24–7.
Itoh, K. et al., "The Effects of High Oral Magnesium Supplementation on Blood Pressure, Serum Lipids and Related Variables in Apparently Healthy Japanese Subjects" *British Journal of Nutrition*, Nov. 1997, 78(5):737–50.
Ryan, M.P., et al., "The Role of Magnesium in the Prevention and Control of Hypertension", *Annals of Clinical Research*, 1984, 16 Suppl 43:81–8.
Widman, L., et al., "The Dose–Dependent Reduction in Blood Pressure Through Administration of Magnesium, A Double Blind Placebo Controlled Cross–Over Study", *American Journal of Hypertension*, Jan. 1993, 6(1):41–5.
Gianni, A.J. et al., "Magnesium Oxide Augmentation of Verapamil Maintenance Therapy in mania", *Psychiatry Research*, Feb. 14, 2000, 93(1):83–7.
Galland, L.D., et al., "Magnesium Deficiency in the Pathogenesis of Mitral Valve Prolapse", *Magnesium*, 1986, 5(3–4):165–74.
Bilbey, D.L., "Muscle Cramps and Magnesium Deficiency: Case Reports", *Canadian Family Physician*, Jul. 1996, 42:1348–51.
Crosby, V., et al., "The Safety and Efficacy of a Single Dose (500 mg or 1g) of Intravenous Magnesium Sulfate in Neuropathic Pain Poorly Responsive to Stong Opioid Anagesics in Patients with Cancer", *Journal of Pain and Symptom Management*, Jan. 2000, 19(1):35–9.
Tanaka, M., et al. "Relief of Neuropathic Pain with Intravenous Magnesium" *Masui. Japanese Journal of Anesthesiology*, Sep. 1998, 47(9):1109–13. Abstract.
Koinig, H., "Magnesium Sulfate Reduces Intra–and Postoperative Analgesic Requirements", *Anesthesia and Analgesia*, Jul. 1998 87(1):206–10.
Facchinetti, F., et al., "Oral Magnesium Successfully Relieves Premenstrual Mood Changes", *Obstetrics and Gynecology*, Aug. 1991 78(2):177–81.
De Souza, M.C., et al., "A Synergistic Effect of a Daily Supplement for 1 Month of 200mg Magnesium Plus 50mg Vitamin B6 for the Relief of Anxiety–Related Premenstrual Symptoms: A Randomized, Double–Blind, Crossover Study," *Journal of Women's Health & Gender–Based Medicine*, Mar. 2000, 9(2):131–9.

(List continued on next page.)

Primary Examiner—John Pak
(74) Attorney, Agent, or Firm—Piper Rudnick LLP

(57) ABSTRACT

A method of treating patients, particularly for pain and/or symptoms of erythromelalgia, and other neurovascular or neuropathic disorders, etc. involves administering high doses of magnesium. The magnesium is introduced through several daily administrations, totaling approximately 2–12 times the RDA for magnesium. These higher levels are achieved through increasing daily dosage amounts gradually in response to patient tolerance and until beneficial results are seen. Total magnesium intake is divided over several doses per day and taken with copious amounts of water.

12 Claims, No Drawings

OTHER PUBLICATIONS

James, M.F., et al., "The Use of Magnesium Sulphate Infusions in the Management of Very Severe Tetanus", *Intensive Care Medicine*, 1985, 11(1):5–12.

Ringvist, I., et al., "Effects of Cold Pressor Test on Circulating Atrial Natriuretic Peptide 99–126 (ANP) in patients with Raynaud's Phenomenon and Influence of Treatment with Magnesium Sulphate and Nifedipine", *Clinical Physiology*, May 1993, 13(3):271–80.

Myrdal, U., et al., "Magnesium Sulphate Infusion Decreases Circulating Calcitonin Gene–Related Peptide (CGRP) in Women with Primary Raynaud's Phenomenon", *Clinical Physiology*, Sep. 1994, 14(5):539–46.

Pfaffenrath, V., et al., "Magnesium in the Prophylaxis of Migraine–A Double Blind Placebo Controlled Study", *Cephalagia*, Oct. 1996, 16(6):436–40.

Belch, J.L. "Temperature–Associated Vascular Disorders: Raynaud's Phenomenon and Erythromelalgia", Chapter 22 in Lowe, GD, Tooke, JE, *A Textbook of Vascular Medicine*, London: Oxford University Press, 1996.

Lepper, J., et al., "Effect of Magnesium Sulfate Infusion on Circulating Levels of Noradrenaline and Neuropeptide–Y–Like Immunoreactivity in Patients with Primary Raynaud's Phenomenon," *Angiology*, Jul. 1994, 45(7):637–45.

Ravn, H.B., "Early Administration of Intravenous Magnesium Inhibits Arterial Thrombus Formation", *Arteriosclerosis, Thrombosis, and Vascular Biology*, Dec. 1997, 17(12):3620–5.

Rauck, R.L., et al., "Refractory diopathic erythrommelalgia", *Anesthesia and Analgesia*, 1996; 82(5):1097–101.

Iseri, L.T. et al., "Magnesium: Nature's Physiologic Calcium Blocker", *American Heart Journal*, 1984; 108(1):188–93.

\* cited by examiner

METHOD OF ADMINISTERING HIGH-DOSE, ORAL MAGNESIUM FOR TREATMENT OF CHRONIC PAIN SYNDROME OF ERYTHROMELALGIA

CROSS-REFERENCE TO RELATED APPLICATIONS

This application claims the benefit of U.S. provisional patent application Ser. No. 60/334,729, filed Nov. 15, 2001.

FIELD OF THE INVENTION

This invention is in the field of oral pharmaceuticals, and especially in pain management.

BACKGROUND

Magnesium is the seventh most plentiful element in the human body and the most common intracellular divalent cation. A cofactor in hundreds of enzymatic processes, including all enzymes utilizing adenosine triphosphate, magnesium's multiple physiologic effects have been recognized for decades. Clinical studies have suggested that magnesium, as a pharmacologic agent, may be beneficial in many disorders including asthma, cardiac arrhythmias, eclampsia, headaches including migraines, hypertension, mania, mitral valve prolapse, muscle cramps, pain syndromes, various menstrual symptoms, seizures, tetanus, and vasospastic disorders. However, the results from various studies have not been unequivocal. These varied results may be due in part to the limited pharmacologic effects of usual oral dosages of 250–500 mg/day, doses that hardly differ from the recommended daily allowances for magnesium of 350 mg/day for women and 420 mg/day for men. The use of higher oral doses has typically been precluded because of magnesium's tendency to provoke diarrhea in many patients when administered orally. For example, in one study a dosage of 250 mg two times daily of magnesium administered orally produced adverse effects in 45.7% of subjects. Yet oral dosing is without question the administration route of choice. Intravenous drug administration requires that the patient be in a hospital or clinic. Where the condition being treated is chronic, this is impractical. Oral administration at pharmacologic doses is key to treating chronic conditions. However oral dosing at pharmacologic levels has heretofore been ineffective due to the inability of patients to tolerate such a regimen.

The inventors have developed a method for successfully introducing high doses of oral magnesium without the tolerance problems previously associated with high oral dosing. This high oral dose magnesium is particularly useful in the treatment of intractable erythromelalgia (EM), neuropathic conditions, and other related neurovascular disorders, and has produced startling results in the management of pain and other symptoms associated with these diseases.

SUMMARY OF THE INVENTION

A method of treating patients, particularly for pain associated with diseases including erythromelalgia, chronic regional pain syndrome, and reflex sympathetic dystrophy, involves orally administering high doses of magnesium. The magnesium is introduced through several daily administrations, totaling approximately 2–12 times the RDA for magnesium (600 mg to 5 gm elemental magnesium). These higher levels are achieved through increasing daily dosage amounts gradually in response to patient tolerance and using a more well-tolerated form of magnesium preferably a magnesium solution. Total magnesium intake is divided over several doses per day and taken with copious amounts of water.

A method for treating a patient with magnesium supplementation comprising:

introducing said patient to a treatment regimen wherein orally administered magnesium dosage levels increase gradually over time from about 250 to 500 mg elemental magnesium/day to between about 600 mg and about 5000 mg/day elemental magnesium, wherein (i) each orally administered daily dosage amount is (a) in extended release form and/or (b) divided into smaller doses and orally administered several times per day, (ii) the orally administered daily dosage amount is gradually increased over time and in association with patient's increased tolerance to the increased dosage, and (iii) the administered magnesium is in a solid form or a solution; and maintaining a well-tolerated high-level dosage of orally administered magnesium until therapeutically effective magnesium supplementation is obtained.

DETAILED DESCRIPTION

Thirteen patients took nonprescription magnesium oxide ($MgO_2$) or magnesium-protein (Mg-protein) products in gradually escalating and divided doses totaling 0.6–5 grams/day elemental magnesium under their physicians' supervision. One patient then took 50%, intravenous-quality magnesium sulfate ($MgSO_4$) orally and reached doses of 12 grams $MgSO_4$/day. Adjusting dose increases to individual tolerance, 8 of the 13 patients obtained substantial pain reduction and improvement in other symptoms with few adverse effects. Over a period of eight months, one patient, who had been bedridden, obtained nearly complete remission and has resumed many normal activities. All patients had been refractory to previous therapies.

The preferred magnesium treatment uses a magnesium compound in solution, such as intravenous grade $MgSO_4$ or MgCl in water or dextrose solution. Other magnesium compounds effective in the present invention include magnesium acetate, magnesium carbonate, magnesium citrate, magnesium gluconate, magnesium glycinate, magnesium hydroxide, magnesium maleate, magnesium orolate, maxnesium oxide, magnesium succinate, magnesium taurate and chelated forms of magnesium with proteins or amino acids. However, other pharmaceutically acceptable forms of magnesium can also be used. The intravenous grade $MgSO_4$ or MgCl may be further diluted with water, before being taken orally. Solid forms of magnesium, such as pills, have also been used. Generally, greater success has been seen when the solid form is ground or pulverized into finely divided material and mixed with water to form a dispersion or suspension or dissolved to form a solution, which is then taken orally. This tends to increase absorption of magnesium in the stomach, reducing the amount of magnesium reaching the colon to cause gastrointestinal distress. Extended release of magnesium can also be used, especially those which remain in the stomach for extended periods of time.

Specifically, it is most important that the magnesium compound (sulfate, oxide, carbonate, etc.) be either very finely divided or dissolved. The dosage needed to achieve reduction of symptoms varies with the sensitivity of the patient. Ideally, dosing should begin at RDA levels and increased as tolerance increases, until pain and/or symptom reduction is achieved. This level can then be maintained longterm. This pain reduction and long term dosing can begin as low as 600 mg elemental Mg/day and may be increased until gastrointestinal distress resulting from administration is consistent. This may occur at a dosage as high as 5 g/day elemental magnesium or even higher. Preferably, at least 1 gm magnesium/day should be administered, more preferably 1.2 gm, more preferably 1.5 gm, still more preferably 2 gm Mg/day. Still more preferably 2.5 gm Mg/day, and most preferably at least 3 gm Mg/day should be administered. To reduce the likelihood of gastrointestinal distress, daily dosages should be divided into several smaller administrations of not more than 500 mg elemental magnesium, preferably not more than 250 mg, and more preferably not more than 150 grams Magnesium per dose. These can be administered several times daily to achieve the correct total daily dose. Small doses taken every 1–2 hours can be used, as can slightly larger doses taken every 4–6 hours. The frequency and size of doses is not as important as the total daily dose, provided the patient can tolerate the regimen.

Also, to reduce the likelihood of gastrointestinal distress, the magnesium should be administered in a highly available form, such as finely divided particles or powder, or more preferably in a solution. Magnesium in the stomach seems to be well tolerated, but as it moves into the intestine, it causes gastrointestinal distress. Thus a form and dosage which can be absorbed by the stomach is preferred. Higher dosages may be used where the magnesium is in solution.

In addition, three patients had previously received nifedipine and/or diltiazem, but the magnesium therapy was more effective and better tolerated. The feasibility and effectiveness of high-dose, well-tolerated oral magnesium therapy suggests the opportunity for therapeutic application in a wide variety of disorders and may serve as a low cost, better tolerated alternative to calcium channel blockers in some patients. The beneficial effects of magnesium therapy in these conditions may be explained by its vascular, sympatholytic, and CNS effects.

Case Studies

Patient #1

This 54 year old male with a chronic undifferentiated autoimmune disorder sustained pressure injuries to both knees. Subsequently he experienced burning pain, especially at night and, months later, paroxysmal infrapatellar hyperemia and increased warmth. A diagnosis of CRPS1 was made. The patient's anti-nuclear antibody was elevated, but repeated x-rays, MRIs, and bone scans were normal. Because of the bilaterality of the symptoms, a diagnosis of erythromelalgia (EM) was also considered. The symptoms of hyperemia, swelling, and pain spread to the patient's lower legs, feet, toes, and to a lesser degree to the thighs, hands, and ears. The patient became intolerant of warmth, had to keep his home below 64 degrees at all times, and applied ice or used cold water immersions to decrease the pain. After 24 months he was completely disabled, bedridden, and in severe pain. Nerve blocks, a sympathetic block, medications (gabapentin, clonazepam, steroids, valproic acid, antihistamines, vasoconstrictors, vasodilators, various opiates), hyperbaric oxygen, physical therapy, and acupuncture provided little or no benefit, or worsened the patient's symptoms.

Based on a report by Belch et al., nifedipine was prescribed, producing the first, albeit limited, improvement in the patient's pain in three years. Adverse effects necessitated a switch to diltiazem, which provided greater, but still limited, benefit. A magnesium treatment regimen was then investigated.

He developed diarrhea with regular doses (~250–500 mg of Magnesium) of standard magnesium supplements, but tolerated doses up to 3 grams/day in divided doses of a nonprescription pharmaccutical-grade magnesium-protein product (MG-Plus protein, Miller pharmacal Inc.). At this dosage, the patient's pain and flaring decreased an estimated 50% within three weeks. After his improvement plateaued, it was discovered that the nonprescription preparation also contained calcium. Hypothesizing that a purer form of magnesium might be more effective, 50% magnesium sulfate ($MgSO_4$) was obtained for intravenous infusion. When the infusions were postponed, small doses of the $MgSO_4$ solution was mixed with water and ingested orally. This solution was tolerated surprisingly well. Increasing very gradually, he was able to reach daily doses of 12 grams $MgSO_4$/day (2.424 gms mg/day) with only occasional, mild adverse effects (loose stools, blurred vision), which were easily controlled by dose adjustment. His CRPS/EM symptoms improved even further and gradually disappeared from his ears, hands, lower legs and feet. Pain was completely eliminated.

He now tolerates temperatures of 80 degrees and can wear socks and shoes again. The marked swelling of his feet has disappeared, as have extension contractures of his toes. He also reports the disappearance of chronic muscle spasms. With only minor residual symptoms, the patient has become active again. This improvement has continued for six months, and the patient now considers himself in nearly total remission from EM, and has been able to reduce his $MgSO_4$ dosage to 4 grams $MgSO_4$/day (808 mg Mg/day).

From a maximum dosage of 12 grams $MgSO_4$/day of magnesium sulfate, patient #1 has been able to gradually reduce the dose to 4 grams $MgSO_4$/day (808 mg/day of elemental Mg). The $MgSO_4$ is a 50% solution for intravenous usage, which the patient measures with a calibrated dropper. Each dose is diluted in approximately 4 ounces of water, and the patient maintains an overall high fluid intake. The patient obtains the most benefit by taking the largest doses of $MgSO_4$ in the morning, when sympathetic activity is maximum. The current regimen is:

6 AM: 1 gram $MgSO_4$
10 AM: 0.5 gram $MgSO_4$
2 PM: 0.5 gram $MgSO_4$
6 PM: 0.5 gram $MgSO_4$
10 PM: 0.5 gram $MgSO_4$
2 AM: 1 gram $MgSO_4$ (time is approximate—the patient typically awakens during the night).

Other Cases

Two patients with EM used escalating doses of magnesium oxide to attain doses of 4–5 grams/day. One, a 30 year old woman, reported not only marked reduction in pain and flaring within two weeks, but also a normal menstruation for the first time in ten years after becoming amenorrheic and developing EM while using oral contraceptives. The other, a 46 year old man with chronic idiopathic polyneuropathy (CIPD), has reported significantly less pain and improved function from severe EM that had rendered him completely bedridden for several years. He has also experienced reduced neuropathic pain from his CIPD. He is now able to walk, drive, and has begun to resume normal activities. Following these responses, other patients with EM were notified about magnesium and, with their physicians' supervision, they initiated high-dose Mg therapy. After 2 months, 11 patients reported their results. Six of the 11 (55%) reported improvement, an impressive result in a population of patients with severe, chronic disease that has been refractory to numerous other treatments. Furthermore, because these patients were only able to obtain over-the-counter solid magnesium products, 5 patients were unable to reach a dose of even 1 gram Magnesium/day because of diarrhea. Of the remaining 6 who were able to reach doses above 1 gram Magnesium/day (1.2 to 7 grams Magnesium/day), 4 patients (67%) improved. One of these patients was able to discontinue all other medications including diltiazem. When the two other, already known cases are added to these numbers, 6 of 8 (75%) of those reaching therapeutic levels of high-dose magnesium obtained benefit.

Pharmacologic Effects of Magnesium

The responses of these patients may be attributable to magnesium's cardiovascular and neurologic effects. Magnesium influences neurochemical transmission, muscular excitability, cardiac conductivity, and peripheral vascular resistance. Magnesium also influences circulating levels of norepinephrine, serotonin synthesis and the synthesis and release of nitric oxide. Magnesium is known to have anti-arrhythmic, anti-seizure, and antiplatelet effects, and to reduce blood pressure and pain.

EM and other neuropathic conditions sometimes respond to treatments that are sympatholytic or otherwise cause selective peripheral vasodilation. Although not reliably effective, vasodialating therapies such as calcium channel blockers, phenoxybenzamine, prostaglandin infusions, long-term epidurals, sympathectomies have been effective in some EM and neuropathic patients. The properties of magnesium—vasodilatory, calcium antagonist, sympatholytic, muscle relaxant—may therefore explain its effectiveness in eight of these thirteen cases. The fact that one patient worsened with magnesium is not surprising in light of his worsening with diltiazem and adds credence to the hypothesis that there are several subtypes of EM. It also is interesting to note that the patient with a diagnosis of CRPS1 had hot-phase, EM-like symptoms. Whether magnesium therapy would be effective in cold-phase CRPS1 characterized by cold, contracted limbs is not known.

Although magnesium's potential benefits for many disorders have been described, patients' lack of tolerance to traditional therapeutic doses has precluded widespread utilization. Indeed, some patients have difficulty tolerating the RDA of magnesium. Five of the patients in this report developed diarrhea with other products before reaching doses of 1 gram/day. In all of the cases presented here, loose stools occasionally developed as doses were gradually increased, but with temporary reductions, accommodation to magnesium's gastrointestinal effects seemed to occur and higher doses became achievable. One patient, unable to tolerate 2 grams of magnesium tablets, reached doses of 4.5 grams/day of magnesium oxide (1.89 g Mg) by blending it in water. All doses were divided and taken at 4–6 hour intervals with copious amounts of water. All patients had normal renal function, which is required for undertaking magnesium therapy.

In addition, patient #1, having partially improved on Mg-protein (2500 mg of elemental Mg) but seeking additional benefit from a more absorbable form of magnesium that was also devoid of calcium, achieved doses up to 12 grams/day of intravenous-grade $MgSO_4$ orally (2020 mg/day elemental Mg). It is speculated that because of the purity and liquidity of this product, upper gastrointestinal absorption was enhanced above the 30–50% absorption of solid products, and relatively little $MgSO_4$ reached the lower intestine or colon. In this patient, repeated chemistries and urine studies were normal. So were his serum magnesium measurements even when taken two hours after ingesting two grams of $MgSO_4$.

Achieving high-dose, oral magnesium therapy in these patients suggests the potential for similar utilization in other cases and other disorders. In addition to the recognized potential uses of magnesium in the conditions listed previously, the improvement of other symptoms in these patients (muscle spasms, contractures, CIPD pain, amenorrhea) suggests additional possibilities (e.g., migraines, diabetic neuropathy, etc.). The development of a maximally tolerable form of magnesium and a standard approach for prescribing it would advance further study and utilization.

Standardization of nomenclature would also be helpful. Standard over-the-counter magnesium products usually provide the total milligrams of the compound rather than the actual milligrams of magnesium, and intravenous $MgSO_4$ is quantified in meq/l (8 meq/l 50% $MgSO_4$=1,000 mg of $MgSO_4$=202 mg elemental magnesium). Some studies use mmols (1 mmol=25 mg elemental Mg). If all labels also provided the milligrams of elemental magnesium, confusion and errors would be reduced.

The fact that two patients found high-dose oral magnesium to be more effective and better tolerated than nifedipine or diltiazem raises other questions. Some authors have called magnesium "nature's physiologic calcium blocker." High-dose, oral magnesium therapy offers a more tolerable, less costly alternative to calcium channel blockers for a broad range of patients.

Of course, physicians inclined to try the methods described above should remember that magnesium has cardiac, CNS, renal, and peripheral effects, and suitable precautions should be taken to obtain appropriate tests and provide adequate supervision of patients prescribed this therapy.

An administration regimen according to the invention allows introduction of greater amounts of magnesium with increased tolerance, and heretofore unknown benefits.

What is claimed is:

1. A method for treating a patient with magnesium supplementation comprising:
   introducing said patient to a treatment regimen wherein orally administered magnesium dosage levels increase gradually over time from about 250 to 500 mg elemental magnesium/day to between about 600 mg and about 5000 mg/day elemental magnesium, wherein (i) each orally administered daily dosage amount is (a) in extended release form and/or (b) divided into smaller doses and orally administered several times per day, (ii) the orally administered daily dosage amount is gradually increased over time and in association with patient's increased tolerance to the increased dosage, and (iii) the administered magnesium is in a solid form or a solution; and
   maintaining a well-tolerated high-level dosage of orally administered magnesium until therapeutically effective magnesium supplementation is obtained.

2. The method of claim 1 wherein said divided smaller doses are administered every 2 to 6 hours.

3. The method according to claim 1 wherein the magnesium is available from at least one of the compounds selected from the group consisting of magnesium chloride, magnesium sulfate, magnesium protein product, and magnesium oxide.

4. The method according to claim 1 wherein solid forms of magnesium are first crushed for dispersion in water.

5. The method according to claim 1 wherein magnesium is available from intravenous grade magnesium sulfate or chloride diluted with water.

6. The method of claim 1 wherein the daily dosage amount is unevenly divided into smaller doses and orally administered several times throughout the day.

7. The method according to claim 6 wherein said magnesium is available from the group consisting of magnesium oxide, magnesium chloride, magnesium sulfate, and magnesium protein product.

8. The method of claim 1 wherein the solid form is an extended release form.

9. The method of claim 1 wherein the solid form is a pill.

10. The method of claim 1 wherein the solid form is very finely divided magnesium.

11. The method of claim 10 wherein the very finely divided magnesium is in a suspension or dispersion.

12. The method of claim 6 wherein the daily dosage amount is unevenly divided into smaller doses and larger of the unevenly divided smaller doses are administered in the morning.

* * * * *